(12) United States Patent
Suzuki

(10) Patent No.: US 7,307,158 B2
(45) Date of Patent: Dec. 11, 2007

(54) SELECTION MARKER GENE

(75) Inventor: Kanako Suzuki, Tokyo (JP)

(73) Assignee: Amano Enzyme Inc., Nagoya-shi (JP)

( * ) Notice: Subject to any disclaimer, the term of this patent is extended or adjusted under 35 U.S.C. 154(b) by 399 days.

(21) Appl. No.: 10/508,694

(22) PCT Filed: Mar. 25, 2003

(86) PCT No.: PCT/JP03/03622

§ 371 (c)(1),
(2), (4) Date: Sep. 28, 2004

(87) PCT Pub. No.: WO03/083109

PCT Pub. Date: Oct. 9, 2003

(65) Prior Publication Data

US 2005/0176148 A1 Aug. 11, 2005

(30) Foreign Application Priority Data

Mar. 29, 2002 (JP) ............................ 2002-094975

(51) Int. Cl.
*C12Q 1/68* (2006.01)
*C12N 1/00* (2006.01)
*C12N 15/00* (2006.01)
*C07H 21/02* (2006.01)
*G01N 33/554* (2006.01)

(52) U.S. Cl. .................... 536/23.1; 435/6; 435/254.11; 435/320.1

(58) Field of Classification Search ...................... None
See application file for complete search history.

(56) References Cited

FOREIGN PATENT DOCUMENTS

| JP | 2000-308491 | 11/2000 |
|---|---|---|
| WO | WO 00/56762 A2 | 9/2000 |

OTHER PUBLICATIONS

Panozzo et al. Aerobic and anaerobic NAD+ metabolism in *Saccharomyces cerevisiae*. FEBS Letters 517: 97-102. 2002.*
P.J. Punt, et al.; "Transformation of *Aspergillus* based on the hygromycin B resistance marker from *Escherichia coli*"; *Gene*; vol. 56; 1987; pp. 117 and 119-124./Discussed in the specification.
T. Kubodera, et al.; "Pyrithiamine Resistance Gene (*ptrA*) of *Aspergillus oryzae*: Cloning, Characterization and Application as a Dominant Selectable Marker for Transformation"; *Biosci. Biotechnol. Biochem.*; vol. 64; No. 7; 2000; pp. 1416-1421./Discussed in the specification.
K. Gomi, et al.; "Integrative Transformation of *Aspergillus oryzae* with a Plasmid Containing the *Aspergillus nidulans argB* Gene"; *Agric. Biol. Chem.*; vol. 51; No. 9; 1987; pp. 2549-2555./Discussed in the specification.
S.E. Unkles, et al.; "The *Aspergillus niger niaD* gene encoding nitrate reductase: upstream nucleotide and amino acid sequence comparisons"; *Gene*; vol. 111; 1992; pp. 149-155./Discussed in the specification.

Y. M.J.T. de Ruiter-Jacobs, et al; "A gene transfer system based on the homologous *pyrG* gene and efficient expression of bacterial genes in *Aspergillus oryzae*"; *Curr Genet*; vol. 16; 1989; pp. 159-163./Discussed in the specification.
K. Iwai, et al.; "Distribution of Quinolinate Phosphoribosyl-Transferase in Animals, Plants and Microorganisms"; *J. Nutr. Sci. Vitaminol.*; vol. 19; 1973; pp. 491-499./Cited in the International Search Report.
H-K. Chang, et al.; "Role of Quinolinate Phosphoribosyl Transferase in Degradation of Phthalate by *Burkholderia cepacia* DBO1"; *Journal of Bacteriology*; vol. 181; No. 10; May 1999; pp. 3069-3070 and 3072-3075./Cited in the International Search Report.
R. Bhatia et al.; "The Sequencing, Expression, Purification, and Steady-State Kinetic Analysis of Quinolinate Phosphoribosyl Transferase from *Escherichia coli*"; *Archives of Biochemistry and Biophysics*; vol. 325; No. 2; Jan. 15, 1996; pp. 270-278./Cited in the International Search Report.
Punt et al.; "Transformation of *Aspergillus* based on the hygromycin B resistance marker from *Escherichia coli*"; Gene; vol. 56; 1987; pp. 117-124; discussed in the specification.
Chang et al.; "Role of Quinolinate Phosphoribosyl Transferase in Degradation of Phthalate by *Burkholderia cepacia* DBO1"; Journal of Bacteriology; vol. 181; No. 10; May 1999; pp. 3069-3075; cited in the International Search Report.
Cullen, Daniel, et al. "Controlled Expression and Secretion of Bovine Chymosin in *Aspergillus nidulans* ;" Bio/Technology, vol. 5, pp. 369-376. (Apr. 1987).
Ballance, D. J., et al. "Development of a high-frequency transforming vector for *Aspergillus nidulans*," Gene, 36, pp. 321-331. (1985).
Tsukagoshi, Norihiro, et al. "Isolation of a cDNA encoding *Aspergillus oryzae* Taka-amylase A: evidence for multiple related genes;" Gene, 84, pp. 319-327. (1989).
Kato, M., et al. "An *Aspergillus nidulans* nuclear protein, AnCP, involved in enhancement of Taka-amylase A gene expression, binds to the CCAAT-containing *taaG2, amdS,* and *gatA* promoters;" Mol Gen Genet, 254, pp. 119-126. (1997).
Kato, N., et al. "Isomaltase formed by α-glucosidases triggers amylase induction in *Aspergillus nidulans*;" Curr Genet, 42, pp. 43-50. (2002).
Kato, M., et al. "No Factors Except for the Hap Complex increase the Taka-amylase A Gene Expression by Binding to the CCAAT Sequence in the Promoter Region;" Biosci. Biotechnol. Biochem., 65 (10), pp. 2340-2342. (2001).
Tani, S., et al. "In Vivo and in Vitro Analyses of the AmyR Binding Site of the *Aspergillus nidulans* agdA Promoter; Requirement of the CGG Direct Repeat for Induction and High Affinity Binding of AmyR;" Biosci. Biotechnol. Biochem., 65 (7), pp. 1568-1574. (2001).

(Continued)

*Primary Examiner*—Nancy Vogel
*Assistant Examiner*—Michele K. Joike
(74) *Attorney, Agent, or Firm*—Edwards Angell Palmer & Dodge LLP

(57) ABSTRACT

It is intended to provide a selection marker gene with the use of auxotrophy as an indication which is usable in transforming a fungus. Namely, a selection marker comprising a quinolinate phosphoribosyltransferase gene isolated from *Aspergillus oryzae*.

6 Claims, No Drawings

OTHER PUBLICATIONS

Berka, R. M., et al.; "*Aspergillus oryzae* EST SEQ ID No. 5364;"(2001) XP-002381185.

Berka, R. M., et al.; "*Aspergillus oryzae* EST SEQ ID No. 4947;"(2002) XP-002381186.

"Nicotinate-nucleotide pyrophosphorylase [carboxylating] (EC 2.4.2.19) (Quinolinate phosphoribosyltransferase [decarboxylating]) (QAPRTase);" (1995) XP-022381187.

"Nicotinate-nucleotide pyrophosphorylase [carboxylating] (EC 2.4.2.19) (Quinolinate phosphoribosyltransferase [decarboxylating]) (QAPRTase) (QPRTase);" (1997) XP-002381188.

The European Search Report dated Jul. 15, 2006, citing references AE, AF, AG & AH.

* cited by examiner

SEQUENCE LISTING

<160> NUMBER OF SEQ ID NOS: 7

<210> SEQ ID NO 1
<211> LENGTH: 1094
<212> TYPE: DNA
<213> ORGANISM: Aspergillus oryzae
<220> FEATURE:
<221> NAME/KEY: CDS
<222> LOCATION: (1)..(156)
<223> OTHER INFORMATION:
<220> FEATURE:
<221> NAME/KEY: CDS
<222> LOCATION: (244)..(300)
<223> OTHER INFORMATION:
<220> FEATURE:
<221> NAME/KEY: CDS
<222> LOCATION: (369)..(1091)
<223> OTHER INFORMATION:

<400> SEQUENCE: 1

```
atg gct tct act tac ggg gac ttc cgt cac ttg cta cct agc aat tac        48
Met Ala Ser Thr Tyr Gly Asp Phe Arg His Leu Leu Pro Ser Asn Tyr
1               5                  10                  15 aaa cgc ctg att act tcc tgg ctc gaa gag gac tgt ccc agt ttt gac        96
Lys Arg Leu Ile Thr Ser Trp Leu Glu Glu Asp Cys Pro Ser Phe Asp
            20                  25                  30 tat ggc ggt ttc gtc gtc ggg gag tca gat ggt gag gca agg ttg ttg       144
Tyr Gly Gly Phe Val Val Gly Glu Ser Asp Gly Glu Ala Arg Leu Leu
        35                  40                  45 ggg aaa gct aag gtaactatca cattccgtgg atgcatgatg aatttgtgtc           196
Gly Lys Ala Lys
    50 tagcgaagta cctatcattg cgtgctaatc catctccgta accatag gga gtc gtt       252
                                                    Gly Val Val
                                                            55 gca ggt gtc cct ttc gtc gat gaa gtt ttc gct cag tta gga tgc acg       300
Ala Gly Val Pro Phe Val Asp Glu Val Phe Ala Gln Leu Gly Cys Thr
                60                  65                  70 tgagtcaatt ccacatgacg ttggacctgg cctgtgccat gcgatcgata tctaaatgac     360 aggaaaga gtg gaa tgg cac gtc caa gaa ggc gag ccc att gaa cct atc      410
         Val Glu Trp His Val Gln Glu Gly Glu Pro Ile Glu Pro Ile
                 75                  80                  85 aaa cat tgc gcc aca gtg cgc ggg cct atc cgc aag atc ctc ctc gga       458
Lys His Cys Ala Thr Val Arg Gly Pro Ile Arg Lys Ile Leu Leu Gly
                90                  95                 100 gaa cgt gtc gcc ctc aat atc ctc gcc cgg tgt tcc ggt atc gca aca       506
Glu Arg Val Ala Leu Asn Ile Leu Ala Arg Cys Ser Gly Ile Ala Thr
            105                 110                 115 aaa agc gcc tcg cta gta gct gct ctc cgt gcc cac gga tgg agt gga       554
Lys Ser Ala Ser Leu Val Ala Ala Leu Arg Ala His Gly Trp Ser Gly
        120                 125                 130 acg ctt gct ggc acc cgt aaa acc acg cct gga ttc cgc gtg gtc gag       602
Thr Leu Ala Gly Thr Arg Lys Thr Thr Pro Gly Phe Arg Val Val Glu
    135                 140                 145 aag tat gga att ctt att gga ggc gcc gat cca cac cgc cat gac ctc       650
Lys Tyr Gly Ile Leu Ile Gly Gly Ala Asp Pro His Arg His Asp Leu
150                 155                 160                 165 agt tcg atg aca atg ctg aag gat aac cac gtc tgg gct tgt gcg aat       698
Ser Ser Met Thr Met Leu Lys Asp Asn His Val Trp Ala Cys Ala Asn
                170                 175                 180 aac cgt gtg gct aag gat ggg gcg ggt cct gct tcg acc gag tcc gtc       746
Asn Arg Val Ala Lys Asp Gly Ala Gly Pro Ala Ser Thr Glu Ser Val
```

-continued

```
Asn Arg Val Ala Lys Asp Gly Ala Gly Pro Ala Ser Thr Glu Ser Val
            185                 190                 195 gcg gct gct ata cct cgg gcg gtt caa gca gct aag gta gct ggc ggc      794
Ala Ala Ala Ile Pro Arg Ala Val Gln Ala Ala Lys Val Ala Gly Gly
            200                 205                 210 ttt gcg acc aag gta gag gtt gaa tgc cga agt gtc gaa gag gcg aat      842
Phe Ala Thr Lys Val Glu Val Glu Cys Arg Ser Val Glu Glu Ala Asn
        215                 220                 225 gcg gct att gag gcc ggg gcg gat gtg atc atg ttg gac aat ttc act      890
Ala Ala Ile Glu Ala Gly Ala Asp Val Ile Met Leu Asp Asn Phe Thr
230                 235                 240                 245 ccg gac ggt gtt cgc gaa gca gct aaa caa ctt aag caa ggt tgg gct      938
Pro Asp Gly Val Arg Glu Ala Ala Lys Gln Leu Lys Gln Gly Trp Ala
            250                 255                 260 gac aag aag caa tcc ttc ctt att gaa gtg agc ggt ggg ttg aac gag      986
Asp Lys Lys Gln Ser Phe Leu Ile Glu Val Ser Gly Gly Leu Asn Glu
            265                 270                 275 tcc aac gct gct tcg tac gcc tgc tcg gac gtc gac att att tcc act     1034
Ser Asn Ala Ala Ser Tyr Ala Cys Ser Asp Val Asp Ile Ile Ser Thr
                280                 285                 290 agc tcg att cac cag ggt gtc ggc att gtg gac ttt tct ctc aag gtt     1082
Ser Ser Ile His Gln Gly Val Gly Ile Val Asp Phe Ser Leu Lys Val
295                 300                 305 tcg ctg cgg tga                                                     1094
Ser Leu Arg
310
```

<210> SEQ ID NO 2
<211> LENGTH: 312
<212> TYPE: PRT
<213> ORGANISM: Aspergillus oryzae

<400> SEQUENCE: 2

```
Met Ala Ser Thr Tyr Gly Asp Phe Arg His Leu Leu Pro Ser Asn Tyr
1               5                   10                  15

Lys Arg Leu Ile Thr Ser Trp Leu Glu Glu Asp Cys Pro Ser Phe Asp
            20                  25                  30

Tyr Gly Gly Phe Val Val Gly Glu Ser Asp Gly Glu Ala Arg Leu Leu
        35                  40                  45

Gly Lys Ala Lys Gly Val Val Ala Gly Val Pro Phe Val Asp Glu Val
    50                  55                  60

Phe Ala Gln Leu Gly Cys Thr Val Glu Trp His Val Gln Glu Gly Glu
65                  70                  75                  80

Pro Ile Glu Pro Ile Lys His Cys Ala Thr Val Arg Gly Pro Ile Arg
                85                  90                  95

Lys Ile Leu Leu Gly Glu Arg Val Ala Leu Asn Ile Leu Ala Arg Cys
            100                 105                 110

Ser Gly Ile Ala Thr Lys Ser Ala Ser Leu Val Ala Ala Leu Arg Ala
        115                 120                 125

His Gly Trp Ser Gly Thr Leu Ala Gly Thr Arg Lys Thr Thr Pro Gly
    130                 135                 140

Phe Arg Val Val Glu Lys Tyr Gly Ile Leu Ile Gly Gly Ala Asp Pro
145                 150                 155                 160

His Arg His Asp Leu Ser Ser Met Thr Met Leu Lys Asp Asn His Val
                165                 170                 175

Trp Ala Cys Ala Asn Asn Arg Val Ala Lys Asp Gly Ala Gly Pro Ala
            180                 185                 190
```

```
Ser Thr Glu Ser Val Ala Ala Ile Pro Arg Ala Val Gln Ala Ala
        195                 200                 205

Lys Val Ala Gly Gly Phe Ala Thr Lys Val Glu Val Glu Cys Arg Ser
    210                 215                 220

Val Glu Glu Ala Asn Ala Ala Ile Glu Ala Gly Ala Asp Val Ile Met
225                 230                 235                 240

Leu Asp Asn Phe Thr Pro Asp Gly Val Arg Glu Ala Ala Lys Gln Leu
                245                 250                 255

Lys Gln Gly Trp Ala Asp Lys Lys Gln Ser Phe Leu Ile Glu Val Ser
            260                 265                 270

Gly Gly Leu Asn Glu Ser Asn Ala Ala Ser Tyr Ala Cys Ser Asp Val
        275                 280                 285

Asp Ile Ile Ser Thr Ser Ser Ile His Gln Val Gly Ile Val Asp
    290                 295                 300

Phe Ser Leu Lys Val Ser Leu Arg
305                 310
```

<210> SEQ ID NO 3
<211> LENGTH: 939
<212> TYPE: DNA
<213> ORGANISM: Aspergillus oryzae

<400> SEQUENCE: 3

```
atggcttcta cttacgggga cttccgtcac ttgctaccta gcaattacaa acgcctgatt    60
acttcctggc tcgaagagga ctgtcccagt tttgactatg gcggtttcgt cgtcggggag   120
tcagatggtg aggcaaggtt gttggggaaa gctaaggagt cgttgcaggt gtcccttttc   180
gtcgatgaag ttttcgctca gttaggatgc acggtggaat ggcacgtcca agaaggcgag   240
cccattgaac ctatcaaaca ttgcgccaca gtgcgcgggc tatccgcaa gatcctcctc    300
ggagaacgtg tcgccctcaa tatcctcgcc cggtgttccg gtatcgcaac aaaaagcgcc   360
tcgctagtag ctgctctccg tgcccacgga tggagtggaa cgcttgctgg cacccgtaaa   420
accacgcctg gattccgcgt ggtcgagaag tatggaattc ttattggagg cgccgatcca   480
caccgccatg acctcagttc gatgacaatg ctgaaggata ccacgtctg ggcttgtgcg    540
aataaccgtg tggctaagga tggggcgggt cctgcttcga ccgagtccgt cgcggctgct   600
atacctcggg cggttcaagc agctaaggta gctggcggct ttgcgaccaa ggtagaggtt   660
gaatgccgaa gtgtcgaaga ggcgaatgcg gctattgagg ccggggcgga tgtgatcatg   720
ttggacaatt tcactccgga cggtgttcgc gaagcagcta acaacttaa gcaaggttgg    780
gctgacaaga agcaatcctt ccttattgaa gtgagcggtg ggttgaacga gtccaacgct   840
gcttcgtacg cctgctcgga cgtcgacatt atttccacta gctcgattca ccagggtgtc   900
ggcattgtgg acttttctct caaggtttcg ctgcggtga                          939
```

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:PCR primer
      for amplifying a DNA fragment unique to a quinolinate
      phosphoribosyltransferase gene

<400> SEQUENCE: 4
gcaatggctt ctacttacgg                                                20

-continued

```
<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:PCR primer
      for amplifying a DNA  fragment unique to a quinolinate
      phosphoribosyltransferase gene

<400> SEQUENCE: 5
ccgcagcgaa accttgagag                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:PCR primer
      for amplifying the cDNA of a quinolinate phosphoribosyltransferase
      gene

<400> SEQUENCE: 6
atccgctgtt caggaagacc                                                  20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:PCR primer
      for amplifying the cDNA of a quinolinate phosphoribosyltransferase
      gene

<400> SEQUENCE: 7
ctcttttact taccgcgtat cc                                               22
```

SELECTION MARKER GENE

TECHNICAL FIELD

This invention is related to a selection marker, which is useful in the genetic engineering technique, and uses thereof. In detail, it is related to a gene encoding a quinolinate phosphoribosyltransferase which is a selection marker being able to be used in transforming a filamentous fungus, a vector containing the gene, a transformant of a filamentous fungus obtainable by transformation with the vector, and a method to produce a protein using the transformant.

BACKGROUND ART

Because *Aspergillus oryzae* included in Genus *Aspergillus* fungi as main members have been used to produce fermented foods or various useful materials since ancient times, and their safety has been proved with the experience of many years, they have recently been utilized broadly as hosts of useful proteins produced by genetic engineering techniques.

In breeding Genus *Aspergillus* fungi for industrial uses, genetic engineering techniques are very effective to confer desired traits to the fungi. In these genetic engineering techniques, a selection marker is necessary to effectively select transformants with desired traits.

The reported selection markers for filamentous fungi are drug-resistant genes such as hygromycin B-resistant gene (Gene. 1987; 56(1): 117-24) or pyrithiamine-resistant gene (Biosci Biotechnol Biochem.; 64(7): 1416-1421 (2000), JP 2000-308491 A); or genes expressing auxotrophy such as argB (Agric. Biol. Chem. 51 (9), 2549-2555, 1987), niaD (Gene 111(2), 149-55, 1992 Feb. 15), or pyrG. (Curr. Genet. 16 (3), 159-163, 1989).

DISCLOSURE OF INVENTION

In general, it is preferable to use selection markers with auxotrophy as indications because the industrial use of microorganisms with antibiotic-resistant genes involves risk of spreading those genes onto the areas of human habitation. But because only limited number of selection markers with auxotrophy as indications have been utilized now, and thus choices are few along the processes of studies, and in some cases, auxotrophy is unstable or selection of markers are not good enough, the development of new selection markers for a filamentous fungus with auxotrophy as indications is strongly desired.

Therefore, the present invention aims to provide a selection marker using auxotrophy as an indication, which is able to be applied in transforming a filamentous fungus. It also aims to provide a vector containing said selection marker gene, a transformant of a filamentous fungus obtained by transformaion with said vector, and a method to produce a protein using said transformant. Further, it aims to provide a filamentous fungus strain which lacks the above-mentioned selection marker gene.

We carried various examinations to solve the above-mentioned problems. First, we mutated an *Aspergillus oryzae* IFO30113 strain (Institute for Fermentation, Osaka), and then isolated the mutant strain which shows auxotrophy and examined its auxotrophy in detail. The result showed that the mutant strain had nicotinic acid-requirement, and it was assumed that this was caused by the lack of quinolinate phosphoribosyltransferase. We then successfully cloned the gene encoding quinolinate phosphoribosyltransferase in *Aspergillus oryzae,* and then confirmed that, when a filamentous fungus strain which lacks the gene was transformed with a plasmid with the gene incorporated, the transformant did not show nicotinic acid-requirement and thus the gene can be used as a selection marker for a filamentous fungus.

The present invention was completed based on the above-mentioned findings, and provides the following constitutions:

[1] A selection marker comprising DNA described in (1), (2), or (3):

(1) DNA which is comprised of the base sequence shown in SEQ ID NO: 1 in the sequence listing;

(2) DNA which is hybridized with DNA comprised of base sequences shown in SEQ ID NO: 1 in the sequence listing under the stringent condition, and which encodes a protein with quinolinate phosphoribosyltransferase activity;

(3) DNA which is comprised of a base sequence obtained by including substitution, deletion, insertion, addition or inversion of one or more bases in the base sequence in SEQ ID NO: 1 in the sequence listing, wherein the base sequences includes, and which encodes a protein with quinolinate phosphoribosyltransferase activity a selection marker which is comprised of DNA described in (1), (2), or (3) below,

[2] A recombinant vector containing the selection marker of [1].

[3] A transformant of a filamentous fungus obtainable by transformation with the recombinant vector of [2].

[4] A method for preparing a transformant, characterized by transforming a filamentous fungus which lacks a quinolinate phosphoribosyltransferase gene with the recombinant vector containing the selection marker of [1], and selecting a transformant using nicotinic acid- or nicotinamide-requirement as an indication.

[5] A method for producing a protein including:

a step for transforming a filamentous fungus which lacks a quinolinate phosphoribosyltransferase gene with the recombinant vector containing the selection marker of [1] and a gene encoding a protein of interest;

a step for selecting a transformant using nicotinic acid- or nicotinamide-requirement as an indication;

a step for culturing the selected transformant under the condition which allows to produce the protein of interest; and a step for recovering the produced protein.

[6] A filamentous fungus strain of *Aspergillus oryzae,* characterized by lacking a gene encoding quinolinate phosphoribosyltransferase.

[7] A recombinant vector containing a quinolinate phosphoribosyltransferase gene derived from a filamentous fungus as a selection marker.

[8] A method for preparing a transformant, characterized by transforming a filamentous fungus which lacks quinolinate phosphoribosyltransferase with the recombinant vector of [7], and selecting a transformant using nicotinic acid- or nicotinamide-requirement as an indication.

[9] A method for producing a protein including:

a step for transforming a filamentous fungus which lacks quinolinate phosphoribosyltransferasegene with a vector containing a quinolinate phosphoribosyltransferase gene derived from a filamentous fungus and a gene encoding a protein of interest;

a step for selecting a transformant according to nicotinic acid- and nicotinamide-requirement as an indication;

a step for culturing the selected transformant under the condition which allows to produce the protein of interest; and a step for recovering the produced protein.

BEST MODE FOR CARRYING OUT THE INVENTION

The constitution of the present invention is described below in detail. The present invention is related to a selection marker, and comprises DNA of the sequence shown in SEQ ID NO: 1 in the sequence listing. This DNA represents a gene encoding quinolinate phosphoribosyltransferase, and can be obtained by the following method.

<1> Isolation of a Gene Encoding Quinolinate Phosphoribosyltransferase in *Aspergillus oryzae*

(1) Acquisition of Nicotinic Acid-requirement Strain of *Aspergillus oryzae*

A gene encoding quinolinate phosphoribosyltransferase is isolated from a chromosome DNA library of *Aspergillus oryzae* (for example, IF030113 strain (Institute for Fermentation)), by PCR reaction using primers which are constructed based on EST clones which are highly homologous to quinolinate phosphoribosyltransferase known in the art, or by hybridization using the PCR products as a probe. Alternatively, the gene encoding quinolinate phosphoribosyltransferase can be obtained by transforming a variant of *Aspergillus oryzae* with nicotinic acid-requirement using a chromosome DNA library or an expression vector of *Aspergillus oryzae*, selecting a transformant to which nicotinic acid-requirement is complemented, and then recovering a recombinant DNA from the transformant.

To verify that the obtained DNA fragment encodes quinolinate phosphoribosyltransferase, one can, for example, transform a host showing nicotinic acid-requirement with the DNA, and then examine that the transformant recovers the nicotinic acid-requirement.

A mutant strain of *Aspergillus oryzae* with nicotinic acid-requirement is obtained by mutating spores of *Aspergillus oryzae* with UV etc. to have a few % of survival rate, and then selecting a strain, which shows nicotinic acid-requirement, from strains which do not grow in a minimal medium. Alternatively, a mutant strain obtained by homologous recombination of the quinolinate phosphoribosyltransferase gene on a chromosome, with quinolinate phosphoribosyltransferase gene into which a mutation is pre-introduced to prevent the gene to be expressed and which is introduced to *Aspergillus oryzae* without nicotinic acid-requirement.

A new method for selecting a transformant with the use of auxotrophy as an indication is provided by using the combination of the filamentous fungus strain and the selection marker gene described above.

(2) Isolation and Identification of the Selection Marker Gene (i) Preparation of a Chromosomal DNA Library of *Aspergillus oryzae*

First, chromosomal DNA is extracted from an *Aspergillus oryzae* (for example, IF030110strain (Institute for Fermentation, Osaka)). The chromosomal DNA is extracted using methods known in the art, for example, a method described in TIG, 10(7), 226 (1994).

The obtained chromosomal DNA is digested with a suitable restriction enzyme (for example, HindIII, EcoRI, EcoRV, PstI, BamHI, and XhoI), and is ligated to the cleavage site of a suitable vector (for example, pUC119, Takara Shuzo Co., Ltd.), which corresponds to the cleavage site of the used restriction enzyme, using a DNA ligase. By transforming a host using the recombinant vector thus obtained, a chromosomal DNA library is prepared.

Any vectors which have ability to replicate autonomously in a host and contain a selection marker can be used, including plasmid pUC119 as well as pUC18, pUC118, pUC19, pBR322.

To prepare a chromosomal library containing full-length genes, it is preferable to apply southern hybridization to chromosomal DNA of *Aspergillus oryzae* which is digested in advance with various restriction enzymes. The restriction enzyme, of which a single band is detected as a result, is used for the preparation of the library.

(ii) Acquisition of Quinolinate Phosphoribosyltransferase Gene from *Aspergillus oryzae*

When cloning a gene encoding quinolinate phosphoribosyltransferase from *Aspergillus oryzae*, a search is performed to find EST clones which have base sequences encoding proteins which are highly homologous to the known quinolinate phosphoribosyltransferase. For EST clone search, for example, *Aspergillus oryzae* EST Database can be used. Oligonucleotides are synthesized based on the base sequences of clones obtained from search which are highly homologous. Oligonucleotides are synthesized using, for example, DNA autosynthesizers which are commercially available. The length of oligonucleotides here is not limited if it is suitable for PCR. The length is 10-50 bases, preferably 15-30 bases. The length is 10-50 bases, preferably 15-30 bases.

Then, part of quinolinate phosphoribosyltransferase gene in *Aspergillus oryzae* is obtained by conducting PCR using the synthesized oligonucleotides as primers and chromosomal DNA of *Aspergillus oryzae* as a template. Using this as a probe, a chromosomal DNA library of *Aspergillus oryzae* prepared in (i) is screened, a clone which contains quinolinate phosphoribosyltransferase gene is selected, and thus a full-length quinolinate phosphoribosyltransferase gene is obtained from the clone.

As a screening method, either colony hybridization or plaque hybridization is used according to the character of the chromosomal library. In particular, when the chromosomal DNA library is prepared using plasmid and its host, *E. coli*, colonies of *E. coli* are transferred to a membrane, and then colony hybridization is performed using part of quinolinate phosphoribosyltransferase gene obtained as above as a probe. By preparing plasmid from clones thus selected, the plasmid with quinolinate phosphoribosyltransferase gene integrated is obtained.

(iii) Analysis of Isolated DNA Fragments (Selection Marker Gene)

The base sequence of the DNA fragment (cloning DNA fragment) which is inserted into the plasmid obtained as described above can be determined by preparing deletion series using, for example, Deletion Kit for Kilo-Sequencing (TAKARA), and then applying ABI PRISM 310 Genetic Analyzer (Applied Biosystems) to the series.

With the method described above, the base sequence (SEQ ID NO: 1) of the coding region of cloning DNA fragment which was obtained from the *Aspergillus oryzae* IF030113 strain (quinolinate phosphoribosyltransferase gene), and the amino acid sequence (SEQ ID NO: 2) which can be coded with this base sequence was determined.

Note that the gene which contains the gene sequence determined here is novel because there has been no other report on the identification of quinolinate phosphoribosyltransferase gene in *Aspergillus oryzae*.

DNA obtained by a partial modification of the sequence in SEQ ID NO: 1 (hereafter, it is also referred as "modified DNA") can still be used as a selection marker of the present invention, as far as the proteins encoded by the DNA contains quinolinate phosphoribosyltransferase activity. Note that, although the level of the quinolinate phosphoribosyltransferase activity is not particularly limited here, the activity is preferably as high as possible considering its function as a selection marker. For example, the activity is preferably substantially equal to the quinolinate phosphoribosyltransferase activity of the protein encoded by the DNA of the sequence of SEQ ID NO: 1.

Examples of the modified DNA include DNA which hybridizes with the DNA of the sequence of SEQ ID NO: 1 under a stringent condition, and which encodes a protein with quinolinate phosphoribosyltransferase activity. Note that a "stringent condition" described herein refers to a condition where specific hybrids are formed but non-specific hybrids are not formed. For example, such a condition includes incubating with a hybridization solution (50% formaldehyde, 10×SSC(0.15M NaCl, 15 mM sodium citrate, pH 7.0), 5× Denhardt solution, 1% SDS, 10% dextran sulfate, 10 μg/ml denatured salmon sperm DNA, 50 mM phosphate buffer (pH7.5)) at a temperature of 42° C., and then washing with 0.1×SSC and 0.1% SDS at 68° C. For a more preferable stringent condition, a condition which uses 50% formaldehyde, 5×SSC(0.15M NaCl, 15 mM sodium citrate, pH7.0), 1× Denhardt solution, 1% SDS, 10% dextransulfate, 10 μg/ml denatured salmon sperm DNA, 50 mM phosphate buffer (pH 7.5)) as a hybridization solution can be exemplified.

Another example of the modified DNA is DNA which is comprised of a base sequence obtained by including substitution, deletion, insertion, addition, or inversion of one or more bases in the base sequence shown in SEQ ID NO: 1, and which encodes a protein with quinolinate phosphoribosyltransferase activity. Mutation such as base substitution can be arisen at plural number of sites. "Plural number" as described herein is 2-40, preferably 2-20, more preferably 2-10, depending on positions of amino acid residues in proteins' conformation or on types of amino acid residues. Note that these modifications include deletion of part of intron, introduction of sequences for digestion by restriction enzymes into 5'-end, 3'-end, or other sites, and addition of sequences encoding signal peptides.

An illustrative example is DNA which has a base sequence without introns, shown in SEQ ID NO: 3.

Modified DNA which encodes a protein that is substantially the same as quinolinate phosphoribosyltransferase described above is obtained by modifying DNA encoding quinolinate phosphoribosyltransferase such that amino acid residues at specific sites contain substitution, deletion, insertion, addition, or inversion using site-directed mutagenesis. Alternatively, it is also obtained using methods which utilize known processes for mutagenesis, such as treating a filamentous fungus containing a quinolinate phosphoribosyltransferase gene with UV and then isolating the modified genes.

Note that mutation of bases such as substitution, deletion, insertion, addition, or inversion described above includes naturally-occurring mutation such as individual differences of microbes containing quinolinate phosphoribosyltransferase, and differences in species or genus.

For example, when such modified DNA is contained in a naturally-occurring filamentous fungus, it can be obtained by extracting genomic (chromosomal) DNA from the fungus, treating this DNA with a suitable restriction enzyme, screening DNA using DNA of SEQ ID NO: 1 or a part thereof as a probe, and then selecting and isolating the DNA which hybridizes to the probe under a stringent condition.

Alternatively, using genomic (chromosomal) DNA library containing clones which retain modified DNA, it can be obtained by screening the library using DNA of SEQ ID NO: 1 or a part thereof as a probe under a stringent condition.

Using the selection marker of the present invention, recombinant vectors for the use of transforming a filamentous fungus can be constructed. In other words, another aspect of the present invention relates to recombinant vectors which contain a selection marker described above. The vectors herein include vectors into which a gene encoding a protein which is desired to be expressed (protein or interest) is pre-incorporated and vectors into which such a gene is not pre-incorporate.

One illustrative method for constructing the recombinant vector is described below.

<2> Construction of Recombinant Vectors

A vector for transforming a filamentous fungus is constructed by inserting the above selection marker gene into a cloning site of a commercially available vector which can be used, for example, to transform a filamentous fungus. The recombinant vector which can be used for the production system of the protein of interest can be obtained by inserting a gene, which encodes a protein which is desired to be expressed (hereafter, it is referred to a "protein of interest"), into the vector which is constructed as above. The types of the proteins of interest herein include, but without limitation, carbohydrate-related enzymes such as α-amylase, glucoamylase, α-glucosidase, cellulase, and pectinase, protease such as chymosin, and lipase. Also, the proteins of interest can be either homogenous proteins or heterogeneous proteins. The homogenous protein means a protein which a filamentous fungus for transformation produces by nature, while the heterogeneous protein means a protein which the filamentous fungus for transformation does not produce by nature, that is a protein which is produced only when a foreign gene which encodes it is introduced to the fungus.

A gene which encodes a protein of interest herein can be used by inserting the gene into a vector without modification when a functional promoter is already contained (e.g. a gene homogenous to the gene in the host). On the other hand, in case of a heterogeneous or homogeneous gene without a promoter, a functional promoter must be connected to the upstream site of the coding region of the protein of interest in the transformant.

A recombinant vector of the present invention includes a vector which at least a part thereof (for example, gene encoding the protein or interest or the selection marker gene) is incorporated into a host chromosome, and one which can be existed as a plasmid in a host.

Insertion of a selection marker into a vector, insertion of a gene encoding a protein of interest, insertion of a promoter, and ligation of a gene encoding the protein of interest and the promoter are performed by conventional techniques.

Considering the ease of preparation of vector DNA, ligation of vector DNA and insertion DNA (construction of a vector), or preparation of a recombinant vector, it is preferable to use a vector which has ability of self-replication in cells of microorganisms such as *E. coli*.

<3> Preparation of Transformant

The recombinant vector described above can be used for transformation of a filamentous fungus. Namely, using the recombinant vector above, a method for preparation of a transformant can be established. Specifically, a method for preparing transformant of a filamentous fungus can be provided, which is characterized by transforming a fungus which lacks a quinolinate phosphoribosyltransferase gene with a recombinant vector which contains the above-mentioned selection marker, and selecting a transformant using nicotinic acid- or nicotinamid-requirement as an indication.

Alternatively, a protein of interest can be produced by culturing a transformant, which is transformed with a recombinant vector into which a gene encoding the protein of interest is inserted, under a condition which allows the structural gene to express. A suitable medium to the host employed is used. For example, a commercially available medium, or a medium which is constructed by addition of elements necessary for growth and for selection for transformants and enhancement of protein expression such as arginine and uridine to the medium can be used.

The protein of interest is recovered from a culture solution or fungus bodies which has been cultured for desired period of time. Namely, a secretory protein is recovered from a culture solution, while other proteins are recovered from fungus bodies. When recovering the protein of interest from a culture solution, it is obtained by filtering and centrifuging the supernatant of the culture to remove insoluble substances, and then isolating and purifying through a combination of precipitation with such as ammonium sulfate, dialysis, and various types of chromatography. On the other hand, when recovering the protein of interest from fungus bodies, it is obtained by crushing the fungus bodies with, for example, pressure treatment or ultrasonic treatment, and then isolating and purifying in the same way as described above. Note that it can also be obtained by recovering the fungus bodies from the culture solution in advance through filtration or centrifugation, and then applying the above-mentioned series of process (crushing the fungus bodies, isolation, and purification).

Types of host filamentous fungus to be used for transformation include, but not limited to, filamentous fungus classified into Genus *Aspergillus* (*Aspergillus oryzae, Aspergillus niger, Aspergillus nidulans*), Genus *Penicillium*, Genus *Tricoderma*, and Genus *Rhizopus*, etc. Preferably, a filamentous fungus in Genus *Aspergillus* fungus is used. *Aspergillus oryzae* and *Aspergillus niger* are especially preferred from the aspect of safety. Note that a host filamentous fungus for transformation must lack a quinolinate phosphoribosyltransferase gene.

Introduction (transformation) of a recombinant vector can be performed by methods known in the art. For example, it can be performed by the method described by Turner et al. (Gene, 36, 321-331(1985)) using protoplasted fungi. Other methods such as the method described by Gomi (Agric. Biol. Chem., 51, 323-328 (1987)) can be employed.

The quinolinate phosphoribosyltransferase described above can be used as a selection marker not only for *Aspergillus oryzae*, but also for fungi in general, because quinolinate phosphoribosyltransferase is an enzyme which acts in the NAD synthesizing pathway, and thus is expected to be highly conserved among species or genera.

Also, a quinolinate phosphoribosyltransferase gene derived from other fungi may be employed as a selection marker for fungi in general in the same way. From these, another aspect of the present invention provides vectors for modifying a filamentous fungus, methods for preparing transformants of fungi, and methods for producing proteins using fungi.

In other words, the vectors are recombinant vectors which contain a quinolinate phosphoribosyltransferase gene derived from a filamentous fungus as a selection marker.

The method for preparing a transformant is characterized by transforming a fungus which lacks quinolinate phosphoribosyltransferase with a recombinant vector containing a quinolinate phosphoribosyltransferase gene derived from a fungus as a selection marker, and selecting a transformant using nicotinic acid- or nicotinamid-requirement as an indication.

The method for producing proteins include transforming a fungus without quinolinate phosphoribosyltransferase gene with a vector containing a quinolinate phosphoribosyltransferase gene derived from a fungus and a gene coding a protein of interest, selecting a transformant using nicotinic acid- or nicotinamid-requirement as an indication, culturing the selected transformant under a condition which allows the protein to be produced, and recovering the produced protein.

The types of vectors which can be utilized herein, the method for constructing vectors, and the method for preparing a filamentous fungus which lacks quinolinate phosphoribosyltransferase are the same as when a quinolinate phosphoribosyltransferase gene of *Aspergillus oryzae* is used. Note that a filamentous fungus described in the present invention means a filamentous fungus in a broad sense, and encompasses yeast.

The invention is further illustrated by the following examples, which should not be construed as further limiting.

In the following examples, restriction enzymes and other enzymes for genetic modification used are products of Takara Shuzo Co., Ltd. and Toyobo Co., Ltd. unless otherwise noted. Note that we followed the manufacturer's instruction for such as conditions for enzymatic reaction.

Also, in the following examples, we used synthetic oligo DNA synethesized by Takara Shuzo Co., Ltd. or Invitrogen, ABI PRISM 310 Genetic Analyzer (Applied Biosystems) for base sequencing, and a thermal cycler (PerkinElmer Japan) for PCR reaction.

For general genetic manipulations, *E. coli* DH5a (Toyobo), Plasmid pUC119 (Takara Shuzo) were used.

EXAMPLE 1

Induction of Mutation

*Aspergillus oryzae* (hereinafter referred to as *A. oryzae*) IFO30113 strain (Institute for Fermentation, Osaka) was inoculated onto a Czapek-Dox medium(0.2% $NaNO_3$, 0.1% $K_2HPO_4$, 0.05% KCl, 0.05% $MgSO_4.7H_2O$, 2% glucose (pH5.5))plate, and then the plate was incubated for 5 days at 30° C. to allow condia to adhere. Adhered condia were suspended into a solution for spore-suspending (0.01% tween80, 0.8% NaCl), and the suspension was filtered through cotton, and then the filtrate was centrifuged at 3000 rpm for 5 minutes to recover the condia. This condia was suspended into 0.8% NaCl solution to become $1 \times 10^7$ spores/ml, and spread on a glass dish, and then mutation was induced by UV irradiation for 1-3 minutes. After UV irradiation, the condia of which mutation was induced were recovered, and then a 92-1 strain, which shows auxotrophy wherein the strain grows in a YPC medium (1% yeast extract, 2% polypeptone, 2% glucose) while it doesn't grow in a Czapek-Dox medium, was isolated.

EXAMPLE 2

Determination of Auxotrophy of *A. oryzae* Strain and Estimation of Deletion Gene Auxotrophy of *A. oryzae* obtained in Example 1 was determined and a deletion gene was estimated. First, three types of plates, each of which 2% casamino acid, 2% yeast extract, or 2% vitamin-free casamino acid (all manufactured by DIFCO) were added to Czapek-Dox media, respectively, were prepared. The 92-1 strain isolated in Example 1 was inoculated punctately onto these plates, and by examining the presence or absence of growth of the variants to find out whether the strain shows amino acid-, nucleic acid-, or vitamin-requirement, it was found out that the strain shows vitamin-requirement.

Next, the spore-suspension of the 92-1 strain was spread over a Czapek-Doxplate, and solutions of thiamin, riboflavin, pyridoxine, calcium pantothenate, para-aminobenzoic acid, nicotinic acid, choline, folic acid, biotin, and inositol were added to the plate dropwise with a pippet, and the reaction of growth of their surroundings was examined. The result showed that it has nicotinic-requirement.

Finally, the 92-1 strain is inoculated onto plates with and without addition of nicotinic acid, and it was confirmed that the presence and/or absence of growth corresponded with the presence and/or absence of nicotinic acid. The examinations described above leaded to determine that the required substance of *A. oryzae* is nicotinic acid.

Examining the metabolic pathway of nicotinic acid, this acid was found out to be one of the constituents of NAD cycle, which was related to NAD synthesis. On the other hand, the 92-1 strain was able to grow on a medium to which nicotinamid, which is located at one position upstream of nicotinic acid in NAD cycle, was added. From these findings, it is assumed that, in the 92-1 strain, every synthetic reaction in NDA cycle is normally implemented, as well as the supply of nicotinic mononucleotide into NAD cycle, namely the synthesis of nicotinic mononucleotide from quinolinic acid is not normally implemented. In other words, the 92-1 strain is assumed to be a strain which lacks a quinolinate phosphoribosyltransferase which is a catalytic enzyme for this reaction.

EXAMPLE 3

Extraction of Chromosomal DNA from *A. oryzae*

The chromosomal DNA from *A. oryzae* IFO30113 strain (Institute for Fermentation, Osaka) was prepared as follows. First, after *A. oryzae* IFO30113 strain was incubated with YPD medium with stirring overnight, the resulted fungus bodies were collected with a Buechner funnel and a No. 2 filter (Advantech), and then washed with sterile water. Extra water was removed from the product, and it was frozen at −80° C. and dried with FREEZONE (LABCONCO). After freeze-drying and then adding 1 mm glass beads, the product was crushed into fine powder by MultiBeads Shoker (YASUI KIKAI) with 2000 rmp for 5 minutes. After an extracting solution (1% hexadecylmetylammonium bromide, 0.7M NaCl, 50 mM Tris-HCl, 10 mM EDTA, 1% β-mercaptoethanol) was added to this fungus powder, the mixture was stirred, and then it was left to stand at a room temperature for 30 minutes. The resulted lysate was extracted with phenol/chloroform to remove protein contamination, and then the equal amount of isopropanol was added to the extract and DNA was precipitated. This precipitate was dissolved into TE solution containing 0.1 mg/ml RNase, and the reaction was carried for 30 minutes at 37° C. Then, additional TE solution containing 0.2 mg/ml proteinase K was added and the reaction was carried for 30 minutes at 37° C. The solution was extracted with phenol/chloroform, and then was made precipitated with 2.5-fold amount of cold ethanol. This precipitate was rinsed with 70% ethanol and dried, and the product was dissoleved in TE solution, which was referred to as a chromosomal DNA solution.

EXAMPLE 4

Synthesis of PCR Fragments Unique to Quinolinate Phosphoribosyltransferase (QPRT) Gene Blast searches were performed using base sequences of *A. oryzae* registered in EST Database, and a base sequence which encodes a protein with high homology to quinolinate phosphoribosyltransferase was searched. Consequently, three clones were found which have base sequences encoding proteins with high homology to putative nicotinic nucleoti de pyrophosphorylase (quinolinate phosphoribosyltransferase) of *Neurospora crassa*. Referring to the base sequences of these clones, primers for preparing PCR fragments unique to quinolinate phosphoribosyltransferase were designed as follows.

```
5'-end primer
QPRT-F: 5'-GCAATGGCTTCTACTTACGG-3'    (SEQ ID NO:4)

3'-end primer
QPRT-R: 5'-CCGCAGCGAAACCTTGAGAG-3'    (SEQ ID NO:5)
```

Using these primers and the chromosomal DNA obtained in Example 3 as templates, 30 PCR cycles were performed providing that 1 cycle is 94° C. for 30 seconds, 54° C. for 30 seconds, and 72° C. for 1 and ½ minute. Then, DNA fragments of about 1100 base pairs were yielded.

EXAMPLE 5

Construction of a Gene Library of *A. oryzae*

First, the chromosomal DNA prepared in Example 3 was reacted with EcoRI, EcoRV, PstI, BamHI, XhoI, HindIII, XbaI, and combinations of each restriction enzyme and EcoRI, and then each reaction was provided for agarose gel electrophoresis. Subsequently, Southern blot analysis was performed using DNA fragments obtained in Example 3 as a probe. Then, it was confirmed that a single band was obtained at around 4800 base pairs by digestion with HindIII.

Next, after digesting chromosomal DNA completely with HindIII, the product was provided for agarose gel electrophoresis, and the fragments of 4500-5000 base pairs in length were collected and purified. These fragments were inserted into a multi-cloning site of pUC119, HindIII, transformed into *E. coli,* and made into a gene library.

EXAMPLE 6

Screening of the Gene Library

QPRT gene was screened from the gene library constructed in Example 5. First, the gene library of *A. oryzae* constructed in Example 5 was screened by colony hybridization using PCR fragments obtained in Example 4 as a probe. Labeling the probe for colony hybridization and signal detection are performed using DIG Nucleic Acid Detection Kit (Roche). The operation was carried out according to the appended instruction.

The screening yielded 20 strains of clones. Plasmids were prepared from each clone, and the sizes and partial base sequences of each of the plasmid were determined. All of these clones had the same plasmid. This plasmid was named pUQ.

EXAMPLE 7

Preparation of cDNA of QPRT Gene (7-1) Extraction of Total RNA from *A. oryzae* IFO30113 Strain The preparation of total RNA from *A. oryzae* IFO30113 strain was carried out as follows. First, after *A. oryzae* was incubated with YPD medium with shaking for 20 hours, the resulted fungus bodies were collected with a Buechner funnel and a No. 2 filter (Advantech), and then washed with sterile water. Extra water was removed from the product, and then the product was crushed into fine powder in liquid nitrogen uging a pestle and mortar. Adding one milliliter of TRIzol reagent (Invitrogen), this crushed fungus was suspended, and transferred to a tube. After leaving at rest for 5 minutes, 0.2 mL of chloroform was added to the suspension with good stirring, and the suspension was left at rest for 3 minutes. This was centrifuged to make separated into upper and lower layers, and the upper layer was transferred into another tube. Subsequently, 0.5 mL of isopropanol was added to the obtained product, and it was left at rest for 10 minutes at a room temperature. After it was centrifuged, supernatant was removed and a gell precipitate was yielded. Adding 1 ml of 75% ethanol into the precipitate with stirring, the mixture was centrifuged. After removing its supernatant and dissolving it into RNase-free water, the total RNA solution was obtained.

(7-2) cDNA Synthesis

In the following RT-PCR operation, SuperScript First-Strand Synthesis System for RT-PCR (Invirtogen) was used. Using the total RNA solution extracted in (7-1), a reaction system was prepared which consists of 1 µl of RNA solution, 1 µl of 10 mM dNTP, 1 µl oligo dT primer, and 7 µl of $H_2O$. After heating this system at 65° C. for 5 minutes, it was quenched and left at rest on ice for 1 minute. Then, after adding 2 µl of 10×RT buffer, 4 µl of 25 mM $MgCl_2$, 2 µl of 0.1M DTT, 1 µl of RNase inhibitor to the mixture, it was left at rest for 2 minutes at 42° C., and then 1 ml of SuperScriptII RT was added to it and reaction was carried out at 42° C. for 50 minutes. Then, after leaving it at 70° C. for 15 minutes, the reaction was stopped, and a First-Strand DNA solution was yielded by adding RNase H and carrying out reaction at 37° C. for 20 minutes. On the other hand, the primers below were synthesized.

```
5'-end primer
QPRT-F2: 5'-ATCCGCTGTTCAGGAAGACC-3'    (SEQ ID NO:6)

3'-end primer
QPRT-R2: 5'-CTCTTTTACTTACCGCGTATCC-3'  (SEQ ID NO:7)
```

Using these primers and the First-Strand DNA prepared as above as templates, 25 PCR cycles were performed providing that 1 cycle is 94° C. for 30 seconds, 54° C. for 30 seconds, and 72° C. for 1 minute and 30 seconds. Then, DNA fragments of about 1000 base pairs were yielded.

EXAMPLE 8

Analysis of the QPRT Gene Sequence

Next, the QPRT gene sequence was analyzed. First, various deletion clones of pUQ obtained in Example 6 were constructed using Deletion Kit for Kilo-Sequencing (TAKARA). Each deletion clone was sequenced and the base sequence over the entire coding region (1094 bp) was determined. Also, cDNA synthesized in Example 7 was sequenced and the entire base sequence (SEQ ID NO: 3) was determined. Comparison between the sequences of pUQ (chromosomal DNA) and cDNA revealed that the QPRT gene contains two introns.

On the other hand, when the base sequence of chromosomal DNA of 92-1 strain which shows nicotinic acid-requirement, an adenine at the 711 position in the QPRT gene (SEQ ID NO:1) was mutated into tymine. With this mutation, a lysine at the 186 position in the amino acid sequence shown in SEQ ID NO:2 was replaced with a stop codon, and thus it was determined that the nicotinic acid-requirement is attributed to this single base replacement.

EXAMPLE 9

Transformation with *A. oryzae* 92-1 Strain as a Host

*A. oryzae* 92-1 Strain was transformed using plasmid pUQ. First, *A. oryzae* 92-1 Strain was incubated in a YPD medium with shaking overnight, and then the obtained fungus was suspended into a cell-wall lytic solution (20 mg/ml Yatalase (Takara Shuzo), 0.8 M NaCl, 10 mM phosphate buffer solution (pH6.0)), and was protoplasted by stirring mildly at 30° C. for 1-2 hours. The yielded protoplasts were filtered through a nylon filter to remove residual fungus bodies. Then, using this protoplasts and pUQ, preparation and transformation of competent cells were performed by the method described by Turner et al. (Gene, 36, 321-331 (1985)), and were grown in a Czapek-Dox medium. As a control group, a transformant using pUC119 was provided in place of pUQ.

Having examined auxotrophy of the transformant, the transformant using pUQ was able to grow in a medium without nicotinic acid. In other words, nicotinic acid-requirement of *A. oryzae* 92-1 strain was disappeared by transformation using pUQ. On the other hand, the control group, the transformant with pUC119, showed nicotinic acid-requirement, and it was not able to grow in a medium without nicotinic acid. From these results, the quinolinate phosphoribosyltransferase gene (QPRT) in pUQ was confirmed to be useful as an effective selection marker against a fungus.

INDUSTRIAL APPLICABILITY

The present invention provides a new selection marker gene which can be used for selecting transformants of filamentous fungi. Also, it provides a fungal strain which lacks the selection marker. The selection marker of the invention is a gene which has a definite expression type suitable for genetic analysis. By using the selection marker of the invention, transformants of filamentous fungi can be selected by the use of nicotinic acid- or nicotinamid-requirement as an indication. Namely, a transforming system can be constructed using requirement of such as nicotinic acid as a indication. Such a transforming system can be used in, for example, genetic technological breeding, analysis of genetic information, and production of proteins using filamentous fungi as hosts.

The invention claimed is:

1. A selection marker comprising DNA described in (1), (2), or (3):
   (1) DNA which is comprised of the base sequence shown in SEQ ID NO: 1 in the sequence listing; or
   (2) DNA which is hybridized with DNA comprised of base sequences shown in SEQ ID NO: 1 in the sequence listing under the stringent condition, and which encodes a protein with quinolinate phosphoribosyltransferase activity; or
   (3) DNA which is comprised of a base sequence without introns, as shown in SEQ ID NO.:3 in the sequence listing.

2. A recombinant vector containing the selection marker of claim 1.

3. A transformant of a filamentous fungus obtainable by transformation with the recombinant vector of claim 2.

4. A method for preparing a transformant, characterized by transforming a filamentous fungus which lacks a quinolinate phosphoribosyltransferase gene with a recombinant vector containing the selection marker of claim 1, and selecting a transformant using nicotinic acid- or nicotinamide-requirement as an indicator.

5. A method for producing a protein including:
   a step for transforming a filamentous fungus which lacks a quinolinate phosphoribosyltransferase gene with a recombinant vector containing the selection marker of claim 1 and a gene encoding a protein of interest;
   a step for selecting a transformant using nicotinic acid- or nicotinamide-requirement as an indicator;
   a step for culturing the selected transformant under the condition which allows for the production the protein of interest; and
   a step for recovering the produced protein.

6. A method for producing a protein including:
   a step for transforming a filamentous fungus which lacks quinolinate phosphoribosyltransferasegene with a vector containing a quinolinate phosphoribosyltransferase gene derived from a filamentous fungus and a gene encoding a protein of interest;
   a step for selecting a transformant according to nicotinic acid- and nicotinamide-requirement as an indicator;
   a step for culturing the selected transformant under the condition which allows for the production of the protein of interest; and
   a step for recovering the produced protein.

* * * * *